United States Patent [19]

Deters

[11] Patent Number: 4,971,188

[45] Date of Patent: Nov. 20, 1990

[54] DEFLECTING ELEMENT FOR A COIN-CHECKING APPARATUS

[75] Inventor: Jürgen Deters, Grossenwöhrden, Fed. Rep. of Germany

[73] Assignee: National Rejectors, Inc. GmbH, Buxtehude, Fed. Rep. of Germany

[21] Appl. No.: 202,825

[22] Filed: Jun. 3, 1988

[30] Foreign Application Priority Data

Jun. 4, 1987 [DE] Fed. Rep. of Germany ....... 3718710

[51] Int. Cl.$^5$ .......................... C07D 5/02; C07D 3/00; G07F 5/02

[52] U.S. Cl. .................................... 194/337; 194/346; 453/15; 29/527.2; 428/458

[58] Field of Search ............... 194/200, 334, 337, 339, 194/340, 341, 344, 346, 350, 353; 453/3, 15; 29/149.5 R, 527.2; 428/458, 461, 463

[56] References Cited

U.S. PATENT DOCUMENTS

| | | | |
|---|---|---|---|
| 2,412,698 | 12/1946 | Van Der Horst | 29/527.2 X |
| 3,108,709 | 10/1963 | Bosmajian | 29/527.2 X |
| 4,263,924 | 4/1981 | Johnson | 194/337 X |

OTHER PUBLICATIONS

Siemens Interest 2000–The New Coinbox Telephone, Goerlitz et al., Telefon Report, vol. 12, No. 1, pp. 36–40, 9-1976.

*Primary Examiner*—Joseph J. Rolla
*Assistant Examiner*—Steve Reiss
*Attorney, Agent, or Firm*—Harness, Dickey & Pierce

[57] ABSTRACT

Deflecting elements and other elements contacting coins in a coin-checking apparatus are provided with plastic bodies which have a hard metallic coating to reduce wear to the exterior surface of the bodies.

6 Claims, 2 Drawing Sheets

FIG. 3
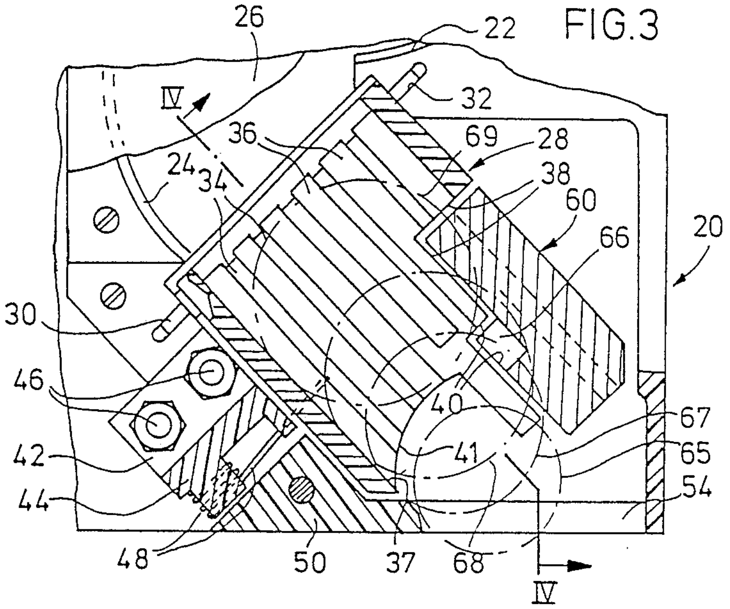
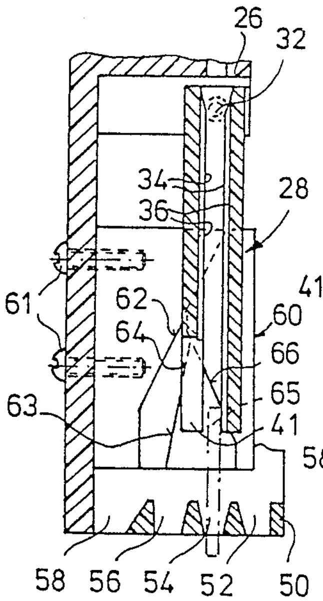
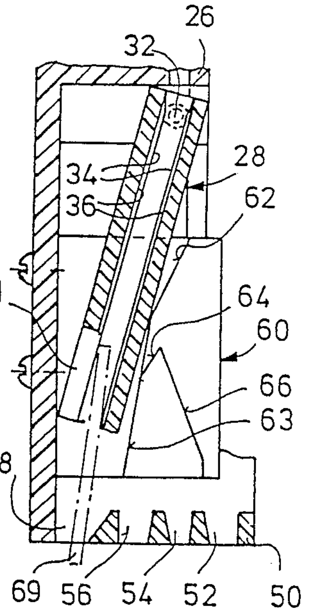
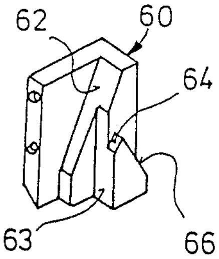
FIG. 6
FIG. 4
FIG. 5

DEFLECTING ELEMENT FOR A COIN-CHECKING APPARATUS

The present invention relates to a track element or deflecting element for coin-checking apparatuses.

In order to conduct a validity check, the coins in a coin-checking apparatus are guided along a compulsory track or passageway. Therefore, so-called track elements are required along which the coins travel, thereby passing for instance sensors or the like. The track elements give the coins a predetermined rolling direction wherein the rolling direction mostly extends in an angle with respect to the direction of the incoming coin. This means that the coin hits the track element with a more or less strong shock. Therefore, it is required to form the track elements of a suitable material which does not undergo a heavy wear by the shock of the coins and thus impair the function of the coin-checking apparatus, even after a long operation period.

Deflecting elements are also found in coin-checking appartuses which are part of coin sorting devices. They are known from German patent letter No. 2 813 183 (European patent equivalent EP No. 4263) and also from German patent No. 2 943 987 (Engligh language equivalent U.S. Pat. No. 4,263,924). Coin sorting devices are necessary when coins of different denomination and size travel the same track or passageway in the coin-checking apparatus. The coin sorting device serves the purpose to consequently distribute the coins among vertical channels according to the denomination of the coins. From the first reference a coin sorting device has become known which operates on a coin deflector comprising a guiding channel. A deflecting element is pivotally mounted on the coin deflector, the deflecting element protruding into a portion of the guiding channel. Coins of a smaller diameter do not move the deflecting element and pass through the guiding channel of the coin deflector into a vertical channel with which the deflector is aligned. Coins of a larger diameter hit the deflecting element and push it out of the guiding channel. This motion of the deflecting element is transferred to a deflecting surface which is secured to the housing of the coin checking apparatus, thereby moving the coin deflector to a predetermined degree for the purpose of aligning it with another vertical coin channel.

In the second reference, a sorting block is provided which is secured to the housing of the coin checking apparatus, the sorting block comprising a plurality of deflecting surfaces which protrude at different distances into the guiding channel of a coin deflector. Depending on the diameter of the coin, the coin cooperates with one of the deflecting surfaces of the sorting block and thereby moves the coin deflector a predetermined degree for the purpose of aligning it with a different vertical coin channel. By means of such a sorting block for instance four coins can be distributed to different vertical channels.

It is known to instruct track elements and deflecting elements of steel. It is also known to temper the surface of the steel, especially for track elements in order to reduce wear. The manufacture of deflecting elements for coin sorting devices is extremely expensive, especially for sorting blocks of the above described type. Heavy wear occurs at deflecting elements made of steel, especially when a tempering of the surface is not provided.

The present invention has the object to provide a deflecting element for coin-checking apparatuses which can be manufactured with little expense and at the same time provides a higher resistance against wear. This object is attained by making the deflecting element of a lighweight, inexpensive, easily formable material which is surface coated with a hard, wear-resistant material.

Preferrably the deflecting element is made of plastic material which is provided with a relatively hard metal layer on its surface by a galvanoplastic process. This metallic layer preferably is a chromium or hard chromium layer.

Chromium-plating of plastic parts per se is known. According to the state of the art, this is, however, accomplished either for optical reasons in order to improve the appearance of the parts or to provide a plastic part with electrical conductivity. In the invention, however, the galvanically applied metallic layer, especially a chromium layer, is provided for the reduction of wear. It has been discovered that in the usual operational life of a vending machine or a coin-checking apparatus having the invention wear of such a deflecting element is minimal. The manufacture of a deflecting element of plastic material and the following galvanoplastic plating process is far less expensive than the manufacture of a deflecting element of steel. It has been discovered surprisingly that a galvanoplastically applied metal layer, especially a chromium layer, can satisfactorily withstand the stresses of the impact of coins hit and that there is no peeling or exfoliation of the chromium layer therefrom. These problems do not occur even with large variations in temperature, although metal and plastic material are known to have much different coefficients of thermal expansion. Furthermore, it has been found as an advantage to form larger, more massive parts used as deflecting elements with cavities in order to minimize the forces which occur at varying temperatures.

The plastic material of which the deflecting element is constructed is relatively resilient, but it has been discovered this resilience does not impair the metal layer applied to by a galvanoplastic process. However, a certain thickness of the layer is necessary, and it is preferably about 0.15 mm.

The plastic material is preferably an acrylic butadien styrene copolymerisate, an acrylic plastic material, a high pressure polyethylene or the like. However, other plastic materials can also be taken into consideration.

The invention will now be described with reference to examples.

FIG. 3 is a side elevation of another coin deflector of a coin sorting device, partly in cross section.

FIG. 4 is a cross section along the line of 4—4 of FIG. 3.

FIG. 5 is the same view as FIG. 4, however, in a different operating position.

FIG. 6 is a perspective view of a sorting block of the sorting device according to the FIGS. 3 to 6.

Figure 2:
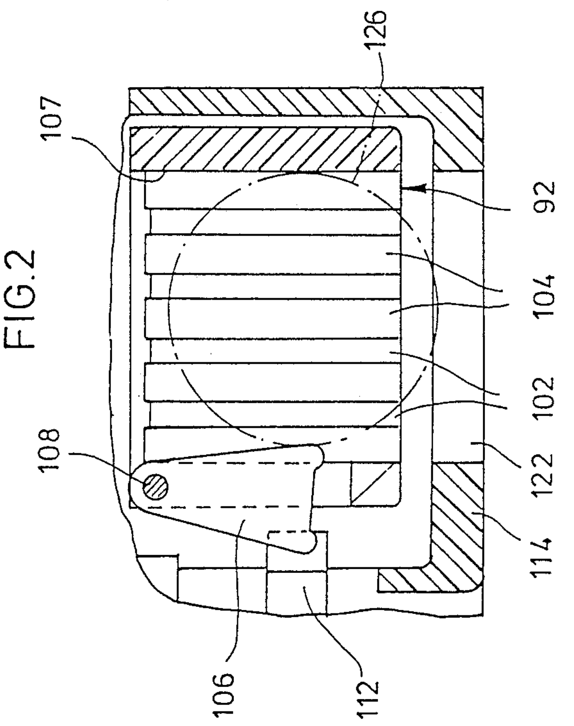
FIG. 2 is a cross section along the line 2—2 of FIG. 1.
Figure 1:
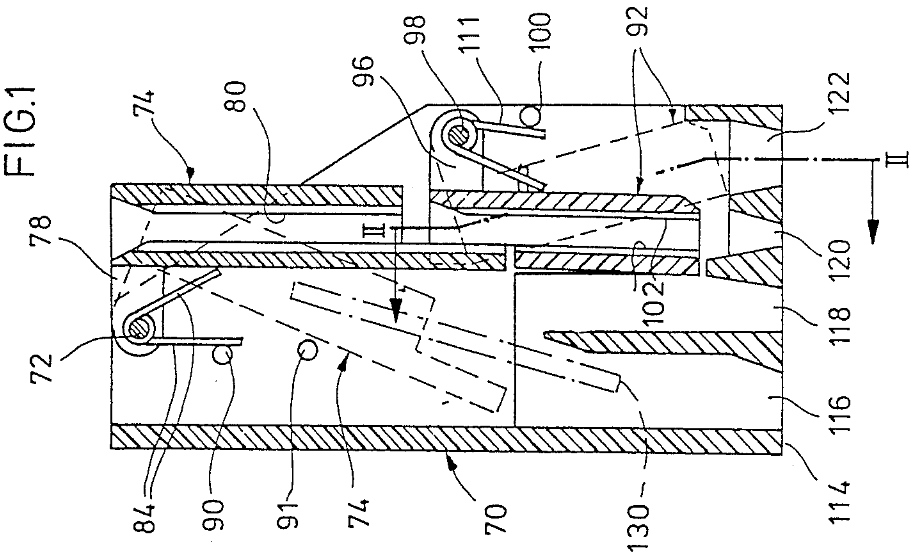
FIG. 1 is a cross section through a coin deflector for a coin sorting device in a coin-checking apparatus.

The sorting device according to FIGS. 1 and 2 is generally designated with 70. A first coin switch 74 is pivotably supported on a hinge pin 72 by arm 78. The coin switch 74 comprises a guiding passage 80 which is defined by a plurality of spaced-apart ribs. The guiding passage for instance is associated with the end of a coin-checking line, and all coins with different diameters initially fall into the guiding passage of the coin switch 74. A spiral spring 84, one arm of which is supported by a stop 90, engages the coin switch 74 counter-clockwise in order to maintain the coin switch in the position shown in FIG. 1 in the normal case. By means of a deflecting element (not shown), the coin switch 74 is pivoted, for instance against a stop 91, as shown in dotted lines in FIG. 1. Thereby, a coin 130 is guided to select a vertical coin channel 116.

Below the coin switch 74, a second coin switch 92 is positioned which is aligned with the coin switch 74 in the normal case. It also comprises a guiding passage which is defined by a plurality of spaced apart ribs. Ribs 102 and apertures 104 between the ribs and shown in FIG. 2. The coin switch 92 is pivotably supported about the pin 98 by means of an arm 96. Coin switch 92 is clockwise engaged by a spiral spring 111, the other arm of the spring 111 supported by a stop 100 which is secured to the housing. In the normal case, the coin switch 92 is biased in the position shown in FIG. 1 and aligned with a vertical coin channel 120. As will be described later, it can be pivoted counter-clockwise in order to guide coins to a vertical coin channel 122. This position of the coin switch is indicated in dotted lines in FIG. 1.

As can be seen in FIG. 2, the coin switch 92 pivotably supports a deflecting element 106 by means of a pin 108, the deflecting element protruding into the guiding passage 102 with one portion. The deflecting element 106 limits the width of the guiding passage as defined between the deflecting element 106 and the wall 107 in the guiding passage. Coins with a diameter smaller than the passage width between the deflecting element 106 and wall 107 fall through into the vertical channel 120 without moving the deflecting element 106. Larger coins 126, however, swivel the deflecting element 106 which itself co-operates with a deflecting surface 112 being secured to the housing of the sorting device and thereby swivels the coin switch 92 to select a position in alignment with a vertical coin channel. A similar deflecting element (not shown) is associated with the coin switch 74 in order to accomplish the described swiveling of the coin switch in the same way. According to the degree of the swiveling an alignment of the coin switch 74 with either the vertical channel 116 and with the vertical coin channel 118 is accomplished. By means of the described sorting device it is therefore possible to sort coins with four different diameters.

The deflecting element 106 for coin switch 92 and also the deflecting element for the coin switch 74 consist of plastic material which by a galvanoplastic plating process, has been provided with a metallic layer on its surface, preferably a chromium or hard chromium layer, respectively, and for instance with a thickness of about 0.15 mm. Thereby, a very wear-proof surface for the deflecting elements is accomplished, so that it does not lose its function during the normal life of a coin-checking apparatus and does not have to be replaced. Also the element 112 which forms the deflecting surface which is secured to the housing can consist of a chromium-plated plastic material as it is subject to relatively severe wear in a similar way.

In an embodiment according to the FIGS. 3 to 5, a coin switch 28 is also pivotably supported by means of pins 30, 32. The coin switch is positioned behind a coin track 24 which can form the exit of a coin-checking line. The coin track 24 is attached to a wall 26 of the coin-checking apparatus. The coin switch 28 again comprises a guiding passage 29 which is aligned with the coin track 24, ribs 34 and grooves 36 alternatively define the guiding passage in the coin switch 28. The one front wall of the guiding passage is designated with the number 37. At the opposite side, an L-shaped recess 38 is formed. Thereunder is an L-shaped recess 40 and an arc-shaped recess at the end of the guiding passage is designated with the number 41. An L-shaped console 42 is attached at the rear wall of the sorting device 20 by means of bolts and nuts 46, and at its cylindrical extension 44, a centering spring 48 is positioned. One leg of the spring 48 co-operates with the front wall of the coin switch 28, while another leg engages behind the rear wall of the coin switch. The legs of the spring keep the coin switch 28 in the position shown in FIG. 4.

Below the coin switch 28, there is a bottom housing portion 50 in which individual vertical coin channels 52 and 58 are positioned with their entrances side by side. The vertical channels 52, 54, 56, and 58 are positioned parallel to each other and may lead to coin-stacking tubes, coin boxes or the like.

A deflecting element 60 is attached at the coin sorting device 20 by means of bolts 61. It is shown in details in FIG. 6. It protrudes into the recesses 38 or 40, respectively, of the coin switch 28. The deflecting element or the sorting 60, respectively, comprises a plurity of deflecting surfaces 62, 63, 64 and 66. With respect to the coin switch 28 they are arranged such that according to the diameter of the coins, the coin switch 28 can be pivoted in various positions with respect to the vertical channels 52 to 58. A certain coin diameter 65 falls down through the guiding passage into the vertical channel 54 without moving the coin switch. Coins with diameters deviating thereof 67, 68, or 69 effect an alignment of the coin switches with the other vertical channels. This principle, however, must not be further described as it has been disclosed in the German patent letter No. 29 43 987 already.

The sorting block 60 consists of plastic material, for instance ABS plastic material, plated with chromium or hard chromium. As the sorting block 60 comprises relatively large dimensions, it is useful to manufacture it with a hollow interior.

The invention was explained with reference to deflecting elements. However, all parts of a coin-checking apparatus can consist of plastic material plated with chromium including also coin tracks which are subject to considerable wear caused by the deflection of coins.

I claim:

1. A coin deflector for use in a coin checking apparatus, said coin deflector being supported for movement by said apparatus when a coin having a predetermined diameter contacts said coin deflector to displace said coin deflector and divert said coin in response to the displacement of said coin deflector into one of a plurality of coin channels, said coin deflector comprising:

(a) a body composed of a plastic material;

(b) a coating on the exterior surface of said body contacted by said coin, said coating applied by a plating process and composed of a hard metallic material substantially resistant to wear from contact with said coin.

2. The coating of claim 1 wherein said metallic material is a chromium-containing material.

3. The coating of claim 1 wherein said metallic material is chromium.

4. The body of claim 1 wherein said plastic material is slected from the group consisting of acrylic plastic and polyethylene plastic.

5. The body of claim 1 wherein said plastic material is an acrylic butadiene styrene copolymer.

6. The coin deflector of claim 1 wherein said body is hollow.

* * * * *